United States Patent [19]
Burg

[11] Patent Number: 5,780,273
[45] Date of Patent: Jul. 14, 1998

[54] INSERTION ELEMENTS AND AMPLIFIABLE NUCLEIC ACIDS

[75] Inventor: J. Lawrence Burg, Framingham, Mass.

[73] Assignee: Amoco Corporation, Chicago, Ill.

[21] Appl. No.: 590,804

[22] Filed: Jan. 24, 1996

Related U.S. Application Data

[63] Continuation of Ser. No. 357,779, Dec. 16, 1994, abandoned, which is a continuation of Ser. No. 45,587, Apr. 9, 1993, abandoned.

[51] Int. Cl.[6] .............................. C12Q 1/68; C12P 19/34; C07H 21/04
[52] U.S. Cl. .......................... 435/91.31; 435/6; 435/91.1; 435/172.3; 435/252.3; 435/320.1; 536/24.1; 536/24.2; 536/24.3; 536/25.3; 935/9; 935/23; 935/16; 935/78; 935/80
[58] Field of Search ................. 536/24.1, 24.2, 536/24.3, 25.3; 435/6, 91.31, 172.3, 252.3, 193, 91.1; 935/23, 9, 77, 78, 80, 116

[56] References Cited

U.S. PATENT DOCUMENTS

| | | | |
|---|---|---|---|
| 4,786,600 | 11/1988 | Kramer et al. | 435/235 |
| 5,112,734 | 5/1992 | Kramer et al. | 435/6 |
| 5,312,728 | 5/1994 | Lizardi et al. | 435/6 |

FOREIGN PATENT DOCUMENTS

| | | |
|---|---|---|
| 0 346 594 A1 | 4/1989 | European Pat. Off. . |
| 0361983 | 4/1990 | European Pat. Off. . |
| WO 91/18117 | 5/1991 | WIPO . |

OTHER PUBLICATIONS

Abstracts from "American Society for Microbiology 93rd General Meeting," *Session 214*, (16–20 May 1993), p. 486.
Klinger, J. D. et al., "Amplified Probe–Based Assays—Possibilities and Challenges in Clinical Microbiology," *Clinical Microbiology Newsletter*, No. 12, 17, (1990), pp. 133–135.
Lomeli, H., et al., "Quantitative Assays Based on the Use of Replicatable Hybridization Probes," *Clinical Chemistry*, vol. 35, No. 9, (Sep. 1989), pp. 1826–1831.
Lizardi, P., et al., "Exponential Amplification of Recombinant–RNA Hybrdization Probes," *Bio/Technology*, vol. 6, (Oct. 1988), pp. 1197–1202, with Abstract.
Miele, E. A., et al., "Autocatalytic Replication of a Recombinant RNA," *Journal of Molecular Biology*, vol. 171, (1983), pp. 281–295.
Lizardi et al Biotechnology (1988) 6: 1197–1202.

*Primary Examiner*—Carla J. Myers
*Attorney, Agent, or Firm*—Norval B. Galloway

[57] ABSTRACT

Novel insertion elements, recombinant molecules and amplifiable nucleic acids and methods for making them are disclosed. The insertion elements and amplifiable nucleic acids can be used with nucleic acid hybridization assays. Also disclosed are libraries of the novel insertion elements, recombinant molecules and amplifiable nucleic acids and the use of such libraries in identifying preferred insertion elements, recombinant molecules and amplifiable nucleic acids of the invention.

21 Claims, 3 Drawing Sheets

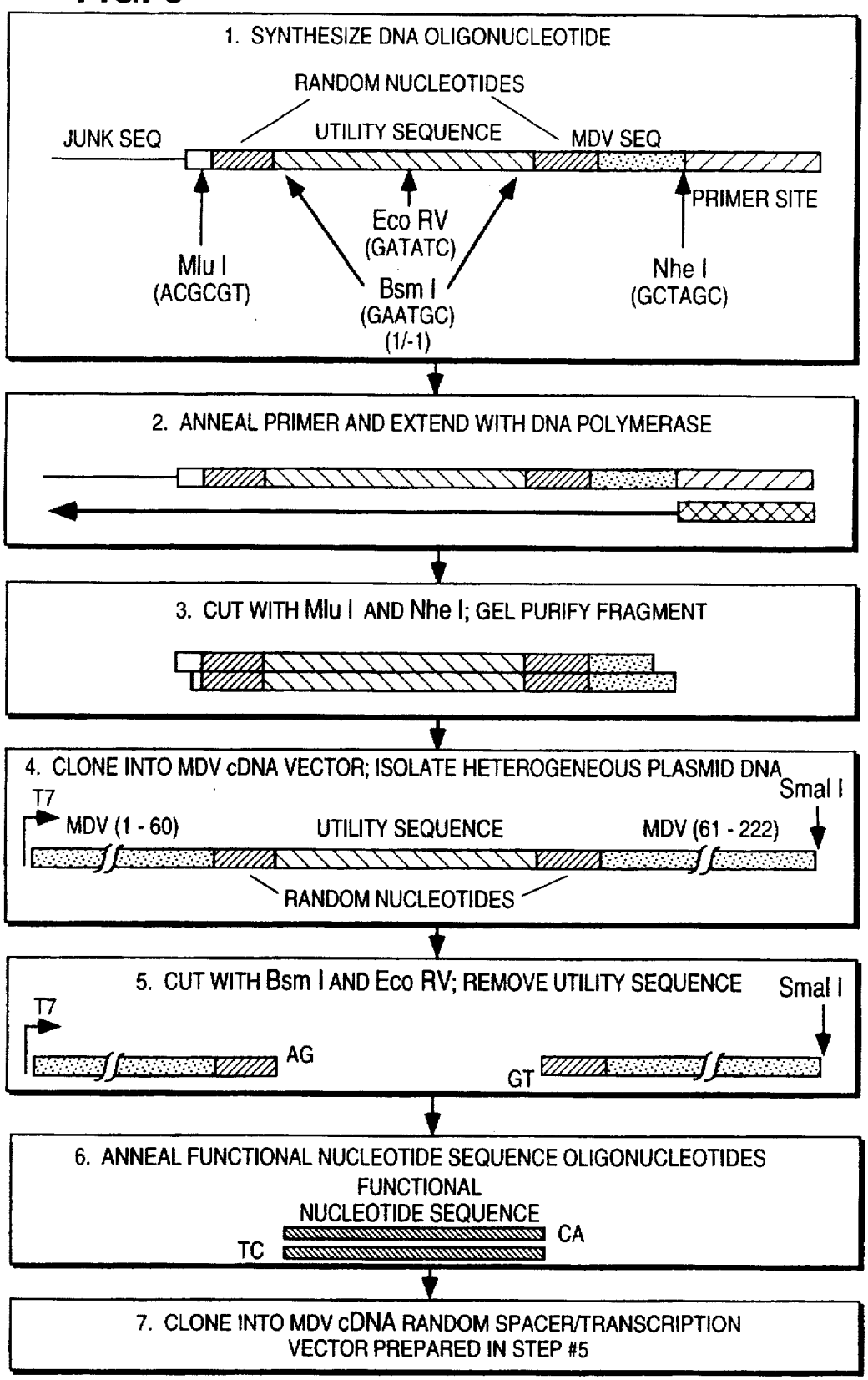

INSERTION ELEMENTS AND AMPLIFIABLE NUCLEIC ACIDS

This is a continuation of application Ser. No. 08/357,779, filed Dec. 16, 1994, now abandoned, which is a continuation of 08/045,587, filed Apr. 9, 1993, now abandoned.

FIELD OF THE INVENTION

The invention relates to insertion elements, recombinant molecules and amplifiable nucleic acids for use with nucleic acid hybridization assays; methods for identifying such insertion elements, recombinant molecules and amplifiable nucleic acids, and methods for making them.

BACKGROUND

The utility of detecting target nucleic acids in clinical diagnostics is well established. Various methods have been developed for detecting specific nucleic acid targets as diagnostic of the presence of a particular organism. These include hybridization assays which rely upon one or more nucleic acid probes designed to hybridize or bind to specific sequences within the target nucleic acid.

The sensitivity of the assay is a concern for all assay formats. Many formats include specific means for enhancing the sensitivity of the basic assay. For example, methods have been developed for amplifying the amount of target present in the sample to be assayed prior to detection. This can be done using a variety of techniques such as the well known polymerase chain reaction (PCR), ligase chain reaction (LCR), multi enzyme amplification reaction (3SR), strand displacement amplification reaction (SDA), and target-dependent replication (TDR).

Assay sensitivity can also be enhanced by amplifying the signal detected. This can be accomplished by monitoring a continuously generated signal over time or increasing the number of labels for detection. This can be accomplished through the use of numerous probes with single labels or the use of probes with numerous labels. Such signals can be readily generated by radioisotopic, enzyme or fluorescent labels attached to an assay probe. These techniques are well known. The assay signal can also be amplified by amplifying the probe to which the label producing the detected signal attaches. This is illustrated for sandwich hybridization assays as follows.

Sandwich hybridization assays typically employ two separate nucleic acid probes. Each probe is designed to hybridize or bind to a mutually exclusive segment within the target nucleic acid. One probe, the detector probe, is constructed to combine with a label moiety. The label moiety is either directly detectable or permits a detectable material to be made. Suitable labels include radio isotopically labelled nucleotides, enzyme/substrate pairs and fluorescent dyes as are well known in the art. The second probe, the capture probe, is constructed to bind to a support in addition to the target. The capture probe is used to isolate the target from extraneous and undesirable materials. Under hybridization or binding conditions, the two probes hybridize with the target to form a capture probe:target:detector probe ternary complex. Addition of a suitable support permits capture of the ternary complex by the support. Thereafter, the complex can be isolated and measured to determine the presence or amount of target present in the sample.

Certain sandwich assay formats use an intercalating fluorescent dye such as propidium iodide in combination with replication of the detector probe to produce the signal. Such assay formats are described in European Patent Application No. 91303739.6 which is incorporated herein by reference. More particularly, these assays can use RNA oligonucleotides or molecules as the detector probe. Following target capture and isolation, the detector probe is replicated enzymatically, e.g., by Qβ replicase, and the replicates allowed to combine with the dye to produce a detectable response.

To be useful in a diagnostic assay, the amplification method must be rapid, sensitive and reproducible. Amplification with Qβ replicase achieves these characteristics with certain nucleic acid substrates. Indeed, Qβ replicase can rapidly and reproducibly replicate and, thus, permit detection of as few as one molecule of such substrates in less than fifteen minutes.

The enzyme Q Beta (Qβ) replicase is considered a template-specific RNA polymerase. The enzyme is obtained from the bacteriophage Qβ. In vivo, the primary function of the enzyme is to replicate the RNA genome of the bacteriophage. Qβ replicase is also known to replicate certain other substrates in vitro. Among these is an RNA termed midivariant RNA or MDV RNA. Midivariant RNA is also referred to as MDV-1 RNA. For purposes of this application, midivariant RNA shall also be considered to include mutant and otherwise modified midivariant RNAs which are rapidly and reproducibly replicated by Qβ replicase.

Significantly, the replication products of Qβ replicase are themselves substrates of Qβ replicase. Thus, replication of these substrates proceeds geometrically providing a powerful means for amplifying the amount of these substrates in a sample. When coupled with a suitable detection system, such amplification permits a powerful diagnostic assay offering the potential of rapid and reproducible detection of as few as one molecule of target.

Qβ replicase is, however, template specific and modifications to an otherwise suitable substrate can seriously degrade the replication properties of the substrate. Thus, MDV RNAs which are initially suitable for replication by Qβ replicase may become unsuitable for replication by Qβ replicase when adapted for use as assay probes and, hence, become unsuitable for use in an assay.

Those in the art have achieved some success in adapting Qβ replicase substrates for use as probes in a diagnostic assay. MDV RNAs, for example, can be adapted to form assay probes by addition of a functional nucleotide sequence at either end or internally to the substrate to permit binding to desirable targets. To date, however, the most success, as measured by retention of the replication properties of the unmodified substrate, has been achieved by introducing the target specific sequence internally to the substrate. As yet, however, those in the art have found no way of determining a priori that a useful target specific sequence can be combined successfully with a substrate to make a useful probe.

Accordingly, there is a need for amplifiable nucleic acids which are adapted from substrates for enzymes such as Qβ replicase and which retain the replication properties of the original substrate. Such amplifiable nucleic acids are adapted to include a functional nucleotide sequence which permits the substrate to bind to a desirable target and, thus, serve as an assay probe.

It is therefore an object of the present invention to produce amplifiable nucleic acids which include a functional nucleotide sequence and are useful for a nucleic acid hybridization assay. Such amplifiable nucleic acids substantially retain the replication properties of the original substrate. It is also an object of the present invention to provide a method for identifying such amplifiable nucleic acids.

SUMMARY OF THE INVENTION

It has now been discovered that insertion elements can be made for use in recombinant molecules such as amplifiable nucleic acids used in nucleic acid hybridization assays. An insertion element of the invention comprises a specific nucleotide sequence which is flanked by one or more spacer elements. The spacer elements generally comprise a sequence of randomly generated nucleotides. If the insertion element is used to construct a probe for hybridizing to a target in a hybridization assay, the functional nucleotide sequence is selected to be able to bind to a separate, target polynucleotide under hybridization conditions. It has also been discovered that the insertion elements of the invention can be incorporated into a replicable nucleic acid substrate such that the replication properties of the substrate are substantially preserved. Thus, a preferred embodiment of the recombinant molecules of the invention is an amplifiable nucleic acid comprising a replicable nucleic acid substrate wherein the nucleic acid substrate further comprises an insertion element of the invention.

It has further been discovered that libraries of such insertion elements, recombinant molecules and amplifiable nucleic acids can be made which greatly facilitate the identification of superior insertion elements, recombinant molecules and amplifiable nucleic acids of the invention. The insertion elements, recombinant molecules, amplifiable nucleic acids and libraries can be made by numerous techniques readily available to the skilled artisan. These include synthesis with automated nucleic acid synthesizers and incorporation of a functional nucleotide sequence into a vector library comprising the randomly generated spacer elements. The functional nucleotide sequences can be inserted into vectors using conventional techniques.

The libraries of the invention are particularly useful in identifying amplifiable nucleic acids for use as probes in a nucleic acid hybridization assay wherein the assay probe is replicated by an enzyme such as Qβ replicase. In many instances, the amplifiable nucleic acids of the invention can be used directly as probes in a nucleic acid hybridization assay. Such assay probes can be replicated rapidly, reproducibly and with great sensitivity, offering the potential for diagnostic assays with a sensitivity of one target molecule.

BRIEF DESCRIPTION OF THE FIGURES

FIG. 3 FIG. 3 presents a schematic representation of a second method for making insertion elements of the invention using Mlu I #61 MDV.

DETAILED DESCRIPTION OF THE INVENTION

Figure 1:
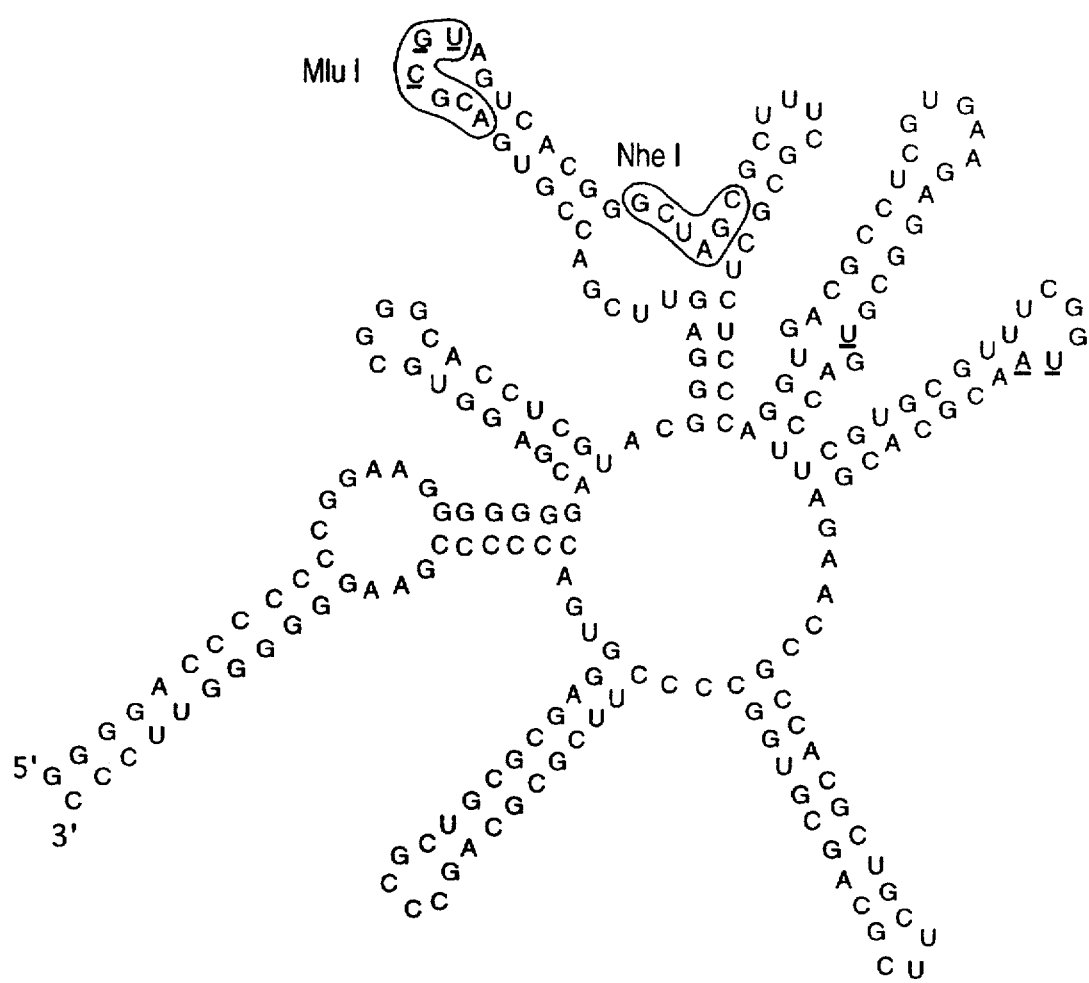
FIG. 1 FIG. 1 presents a nucleotide map of Mlu I #61 MDV.

It has now been discovered that recombinant molecules with particularly useful properties can be obtained if the recombinant molecules are adapted to comprise an insertion element of the invention. Such insertion elements comprise a functional nucleotide sequence flanked by one or more spacer elements. A preferred embodiment of the recombinant molecules of the invention is an amplifiable nucleic acid with excellent replication properties for use in a diagnostic assay. The novel amplifiable nucleic acid comprise a novel insertion element incorporated into a replicable nucleic acid substrate. A novel insertion element of the invention comprises a functional nucleotide sequence flanked on either side by one or more spacer elements. The spacer elements generally comprise a sequence of randomly generated nucleotides. The replicable nucleic acid substrates and, hence, the novel amplifiable nucleic acids are replicable by enzymes such as Qβ replicase. The amplifiable nucleic acids and insertion elements can be RNAs or DNAs.

Amplifiable nucleic acids are preferably constructed such that the functional nucleotide sequence and flanking spacer element(s) are introduced within the nucleic acid substrate rather than appended to either end of the nucleic acid substrate. Examples of such substrates include the following substrates for the enzyme Qβ replicase: MDV RNA, Qβ phage RNA, CT RNA, WS-1 RNA, microvariant RNA, RQ120 RNA, RQ135 RNA and functional equivalents and fragments of these. Qβ replicase is also known to replicate DNA. Other enzyme/substrate combinations include T7 RNA polymerase and its substrates X and Y RNA. RNA polymerase from other RNA bacteriophages such as R17, f2, MS2, fr, M12, SP and μ2 are expected to have similar utility.

More broadly, the insertion elements of the invention are used to insert a functional nucleotide sequence into a host molecule to form a recombinant molecule of the invention. In addition to the hosts described above for amplifiable nucleic acids, suitable hosts include chromosomal and extrachromosomal DNA and RNA species such as hnRNA, mRNA, rRNA, tRNAs and snRNAs. Additionally, insertion elements may be inserted into the RNA genomes of RNA bacteriophages such as R17, f2, MS2, fr, M12, SP and μ2 and other substrates of the RNA polymerases of these organisms. Insertion elements may also be inserted into the RNA genomes and their satellite RNAs of RNA viruses of plant and animal cells.

The insertion elements enable a functional nucleotide sequence to be inserted advantageously into host molecules where direct insertion of the functional nucleotide sequence proves deleterious to the host, e.g., when otherwise desirable properties of the host are lost or degraded due to addition of the functional nucleotide sequence. In general, the spacer elements are believed to relieve structural stresses imposed upon the host by addition of the functional nucleotide sequence.

The insertion elements are shown herein to facilitate enzymatic replication of a host nucleic acid. Insertion elements are also expected to stabilize the functional nucleotide sequence within the host. Thus, the spacer elements are expected to prevent or diminish deletions or alterations of the functional nucleotide sequence during replication or other uses.

Insertion elements may also be used to insert a functional nucleotide sequence into a gene that encodes for a specific protein. The functional nucleotide sequence may be used to add or modify the amino acid structure of the protein. The insertion elements may be used to stabilize an mRNA transcript of the modified gene.

Insertion elements may also be used to augment the functionality of the functional nucleotide sequence. For example, when a ribozyme is used as a functional nucleotide sequence, spacer elements can be used to enhance or stabilize the interaction between the ribozyme and its RNA substrate.

The insertion elements of the invention are discussed and illustrated herein in terms of their utility with amplifiable nucleic acids used as probes in nucleic acid hybridization assays. However, the insertion elements permit much broader applications. For example, an insertion element can be used to insert a functional nucleotide sequence into a host molecule which then serves as a target for a labeled probe. The inserted functional nucleotide sequence may also serve as a binding partner for a protein, an anti-nucleic acid antibody or other ligand.

When an amplifiable nucleic acid of the invention is to be used as a probe in a hybridization assay, the functional nucleotide sequence will be constructed to achieve the binding characteristics required of the sequence. As is well known in the art, this is typically determined by the conditions of a hybridization assay in which a probe incorporating the functional nucleotide sequence will be used. For example, the functional nucleotide sequence can be designed to bind to a polynucleotide sequence which is specific for a single target species or to bind more generally to a polynucleotide sequence which is specific for a multiplicity of targets. The functional nucleotide sequence can also be designed to bind to a nucleotide sequence which is merely characteristic of the assay target(s) and not specific to the target(s).

When used in a hybridization assay, the functional nucleotide sequence will typically comprise an oligonucleotide complementary to a segment of the separate, target polynucleotide. As is known in the art, the degree of complementarity required of the functional nucleotide sequence depends upon the conditions under which the binding or hybridization will be induced. The degree of complementarity will depend, for example, upon the temperature during hybridization, sample reagents (e.g., salt content and the nature of the salts employed), required kinetics and other conditions well known in the art. While perfect complementarity between a functional nucleotide sequence and an assay target is often desirable, perfect complementarity is also often not obtainable and often not desirable. Moreover, the binding characteristics required of the assay probe depend upon the function of the probe in the assay. In a sandwich assay, for example, the capture probe and detector probe perform different functions and the binding characteristics required of each probe may differ accordingly. More particularly, the capture probe can be designed to bind very specifically to the target while the detector probe is designed to bind to the target but with much less specificity. The specificity of the assay toward the target is then determined by the capture probe and not by the detector probe.

Similarly, the length of the functional nucleotide sequence depends upon the functional characteristics required of the sequence nucleotide. When used in probes for hybridization assays, however, functional nucleotide sequences are typically from about 8 to 60 nucleotides in length. Certainly, longer functional nucleotide sequences can be utilized as is known in the art. Numerous functional nucleotide sequences for numerous assay targets have been identified by those skilled in the art. Similarly, methods have been developed by those skilled in the art for identifying additional functional nucleotide sequences for new or known assay targets as such become desirable.

Once a suitable functional nucleotide sequence has been identified, the functional nucleotide sequence can be adapted for use in an assay probe. If the assay format requires amplification of the assay probe, care must be taken to insure that the assay probe is sufficiently amplifiable.

It is known, for example, that native MDV RNA is an excellent substrate for Qβ replicase and can be replicated rapidly, reproducibly and with great sensitivity by the enzyme. Thus, it is desirable to adapt MDV RNA for use as an amplifiable probe in a diagnostic assay. This requires that MDV RNA be modified to include a functional nucleotide sequence. However, the replicability of MDV RNA often degrades considerably when it is modified to include an exogenous nucleotide sequence. Thus, a means for preserving in an adapted substrate the excellent replication properties of the native substrate is desirable. Similarly, a means for rapidly and methodically identifying amplifiable nucleic acids, i.e., replicable substrates adapted to include functional nucleotide sequences, with excellent replication properties is also desirable. The insertion elements and amplifiable nucleic acids of the invention permit these objects to be met. The insertion elements and amplifiable nucleic acids are readily constructed and those with excellent replication properties are readily identified.

It has been discovered that much of the excellent replication properties of a replicable nucleic acid substrate can be retained notwithstanding incorporation of a functional nucleotide sequence into the substrate if the functional nucleotide sequence is incorporated as an insertion element of the invention. That is, excellent replication properties can be retained if the functional nucleotide sequence is flanked by one or more spacer elements comprising a sequence of randomly generated nucleotides. The nucleic acid substrate so modified is an amplifiable nucleic acid of the invention.

Each spacer element of the invention comprises a separate sequence of nucleotides. Presently the sequences of nucleotides are selected randomly. By random selection is meant that each nucleotide of the spacer element is selected without direct correlation to any other nucleotide of the spacer element. Similarly, the individual nucleotides of a spacer element are selected without direct correlation to the functional nucleotide sequence which will be flanked by the spacer element. It is understood, however, that completed insertion elements will be screened to identify those which confer optimal properties. For example, when insertion elements are used in amplifiable nucleic acids, the amplifiable nucleic acids will be screened to identify those combinations of spacer elements and functional nucleic acid sequences which provide amplifiable nucleic acids with optimal replication properties. Thereafter, large quantities of the optimal amplifiable nucleic acid can be prepared.

A sequence of random nucleotides can be generated, for example, by programming an automated nucleic acid synthesizer to select nucleotides randomly from an equimolar mixture of nucleotide triphosphates. Those skilled in the art will understand that additional methods are readily available for generating random sequences of nucleotides.

The length of a spacer element is limited only by its ability to permit useful properties in the recombinant molecule of the invention. For an amplifiable nucleic acid of the invention a spacer element is limited by its ability to permit useful replication properties. Thus, spacer elements are at least 2 nucleotides in length. Presently, spacer elements of from 2 to 25 nucleotides are preferred for amplifiable nucleic acids. Spacer elements of from 8 to 14 nucleotides are most preferred.

It is intended that the spacer element(s) flank the functional nucleotide sequence within the recombinant molecule. It is preferred that spacer elements are immediately adjacent to the functional nucleotide sequence. Additionally, spacer elements should not be more than about ten nucleotides away from the functional nucleotide sequence. The invention contemplates the use of at least one spacer element flanking the functional nucleotide sequence. If a single spacer element is used, the spacer element may lie either 3' or 5' to the functional nucleotide sequence. When two or more spacer elements are used. it is preferred that the functional nucleotide sequence be flanked on each side by at least one spacer element.

Numerous insertion elements and amplifiable nucleic acids with excellent replication properties have been found. It has also been found, however, that the spacer elements are of specific rather than general utility. That is, a spacer element may combine with one functional nucleotide sequence and nucleic acid substrate to form an amplifiable nucleic acid with excellent replication properties, but the same spacer element may not combine with another functional nucleotide sequence and nucleic acid substrate to form an amplifiable nucleic acid with similarly excellent replication properties. Thus, useful spacer elements must be identified for each functional nucleotide sequence and nucleic acid substrate to be used in an amplifiable nucleic acid.

The frequency of spacer element/functional nucleotide sequence/nucleic acid substrate matches which provide amplifiable nucleic acids with excellent replication properties varies with several factors including the spacer elements, functional nucleotide sequence and nucleic acid substrates, the conditions under which replication will occur and the replication properties required (kinetics, sensitivity, reproducibility, etc.). Thus, an important aspect of the invention is the construction of libraries of amplifiable nucleic acids and insertion elements of the invention for each functional nucleotide sequence of interest. The members of a library typically differ only in the spacer element(s) of their respective insertion elements. Construction of libraries of insertion elements and amplifiable nucleic acids permits rapid and convenient construction and identification of preferred insertion elements and amplifiable nucleic acids of the invention.

In principle, the number of members making up a library is limited only by the number of possible spacer element combinations considered. For example, a single spacer element of ten nucleotides permits a library of over one million members. In practice, however, the number of members constructed for a library is limited by more practical considerations such as the time required to construct and separate the individual library members and the efficiencies of each step in the construction process. Moreover, the time required to evaluate library numbers is typically such that only a relatively few library members are evaluated. For example, although libraries of over 100,000 members are readily made, only about 20 to 50 members are typically evaluated. Thus, useful libraries can comprise as few as about 20 to 50 members. Those skilled in the art will appreciate that numerous methods are available for constructing insertion elements, amplifiable nucleic acids and libraries of them. Two such methods are described herein.

Methods For Making Insertion elements, Amplifiable Nucleic Acids And Libraries The methods described here demonstrate the production of amplifiable nucleic acids which are superbly replicated by Qβ replicase. The methods reference the use of engineered midivariant RNA and DNA referred to herein as Mlu I #61 and illustrate the preparation of insertion elements with two spacer elements on either side of the functional nucleotide sequence. However, the methods are of general utility and can be adapted to produce insertion elements and amplifiable nucleic acids with one or more spacer elements for other engineered MDVs and alternative insertion sites. The methods are also applicable to other replicable substrates.

Midivariant RNA is a well studied 222 nucleotide RNA that is rapidly and reproducibly replicated by Qβ replicase. Mlu I #61 is derived from native MDV RNA by inserting a CGU sequence between bases 63 and 64 of native MDV RNA. At the DNA level, this insertion introduces a unique restriction site (ACG CGT. Seq. ID #1) for the enzyme Mlu I beginning at base 61 of the RNA. Additionally, the nucleotides U, U and A are substituted at bases 117, 136 and 137. FIG. 1 shows a nucleotide map of Mlu I #61. Conventional symbols are used to represent all nucleotide bases referenced herein: A represents adenine, T thymine, U uracil. G guanine and C cytosine. Mlu I #61 RNA can be produced in various ways as is known by those skilled in the art. One method is described in the Examples.

Figure 2:
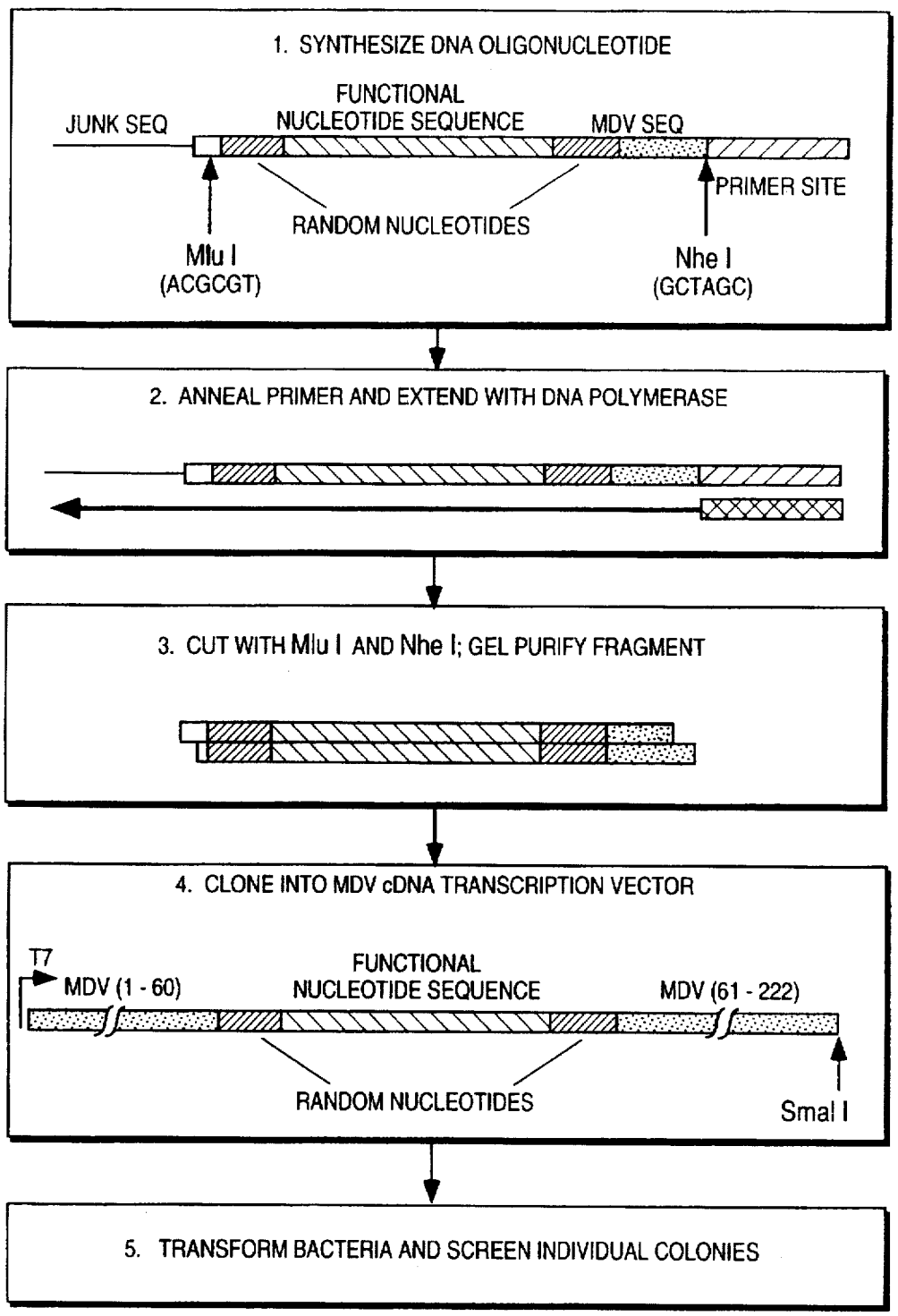
FIG. 2 FIG. 2 presents a schematic representation of one method for making insertion elements of the invention using Mlu I #61 MDV.

A. One method for making a library of amplifiable nucleic acids including a functional nucleotide sequence flanked by two spacer elements is shown schematically in FIG. 2. In this method, a DNA oligonucleotide comprising an insertion element is synthesized to include the following segments: (1) a specific but arbitrary (junk) sequence; (2) the Mlu I recognition site (ACG CGT, Seq. ID #1); (3) A first spacer element of random nucleotides; (4) a functional nucleotide sequence; (5) a second spacer element of random nucleotides; (6) the nucleotide sequence AGT CAC GG (Seq. ID #2) which is the sequence between the Mlu I and Nhe I sites of MDV; (7) the Nhe I recognition sequence (GCT AGC. Seq. ID #3); and (8) a primer binding site to permit formulation of double stranded DNA.

The arbitrary sequence (1) is also referred to as a "junk" sequence. The junk sequence serves at least two purposes. First, it serves to keep the Mlu I site from being at the extreme end of the double stranded DNA produced by an extension reaction which converts the single stranded oligonucleotide into double stranded DNA. This is desirable because many restriction enzymes cleave DNA inefficiently when the restriction site is at or near the end of a double stranded DNA molecule. The junk sequence also allows determination that the Mlu I cleavage has occurred. Cleavage can be detected because the extended DNA will be reduced in size by the length of the junk sequence and the junk sequence fragment will appear as a reaction product. The junk sequence can be of any length but is preferably between 5 and 20 nucleotides in length.

The nucleotides making up the spacer elements (3) and (5) are chosen randomly. The spacer elements can be of any length but are preferably 2 to 25 nucleotides in length. The functional nucleotide sequence (4) is chosen to achieve the binding specificity required of the amplifiable nucleic acid.

The primer binding site can be any nucleotide sequence for which a complementary oligonucleotide primer is available or can be synthesized. However, the primer and primer binding site are chosen such that the primer itself does not bind to any other portion of the DNA oligonucleotide under construction. Preferable primer binding sites are typically about 15 to 30 nucleotides in length. These include sequences comprising the well known T7 and SP6 promoters for which primers are readily available.

Typically, such oligonucleotides total one hundred or more nucleotides in length. For example, when the insertion element comprises a junk sequence of 21 nucleotides, two spacer elements of 10 nucleotides each, a functional nucleotide sequence of 35 nucleotides, and a primer binding site of 27 nucleotides, the insertion element is 122 nucleotides long. Models of such insertion elements are as follows:

```
5'    GCT CAT CTG AGT CAT CCA AGT ACG CGT NNN NNN NNN NAG GCC TTT
ACC CCA CCA ACT AGC TGA TAT CAC ATA NNN NNN NNN NAG TCA CGG GCT
AGC CCT ATA GTG AGT CGT ATT AGC AAG CT 3' (Seq. ID #4).
```

The insertion element includes two spacer elements of ten nucleotides each. These are represented by the two blocks of Ns where N is G, A, T or C in equal probability. The two spacer elements flank a 35 nucleotide functional nucleotide sequence which binds to the 16S rRNA of *Chlamydia trachomatis* under appropriate hybridization conditions.

```
5'    GCT CAT CTG AGT CAT CCA AGT ACG CGT NNN NNN NNN NCT GCT GCC
TCC CGT AGG AGT TTG GGC CGT GTC TCA GTT CCA GTG TNN NNN NNN NNA
GTC ACG GGC TAG CCC TAT AGT GAG TCG TAT TAG CAA GCT 3' (Seq. ID #5)
``` where N is G,A,T or C in equal probability. The insertion element includes two spacer elements of ten nucleotides each and a 45 nucleotide functional nucleotide sequence which binds to the 16S rRNA of most eubacteria under appropriate hybridization conditions.

```
5'    GCT CAT CTG AGT CAT CCA AGT ACG CGT NNN NNN NNN NTG GTG CCC
TTC CGT CAA TTT CTT TAA GTT TCA GCC TTG CGN NNN NNN NNN AGT CAC
GGG CTA GCC CTA TAG TGA GTC GTA TTA GCA AGC T 3' (Seq. ID #6)
``` where N is G,A,T or C in equal probability. The insertion element includes two spacer elements of ten nucleotides each and a 40 nucleotide functional nucleotide sequence which binds to the 18S rRNA of most fungi under appropriate hybridization conditions..

Specific insertion elements can be made using conventional oligonucleotide synthesis techniques and commercially available nucleic acid synthesizers. A library of such insertion elements is made for incorporation into a plasmid DNA Vector. The library should include as many insertion elements as is practicable. However, the number of insertion elements synthesized will be limited by practical considerations such as the efficiencies of the separate steps required for constructing the insertion elements and the libraries. Typically, libraries of about 100,000 insertion elements or amplifiable nucleic acids are made. Plainly, insertion elements can be made and evaluated on an individual basis. However, the systematic synthesis and evaluation of individual insertion elements is intended to be the synthesis and evaluation of a library of the invention.

The insertion elements can be incorporated into replicable nucleic acid substrates to form amplifiable nucleic acids which are then incorporated into suitable vectors to form a library as follows. The vectors can be made by cloning MDV DNA into a suitable plasmid vector such as commercially available pBR322 pUC19 plasmids. Other suitable plasmids are the commercially available pGEM and pBluescript II plasmids. These contain or can be modified to contain a suitable promoter sequence. The promoter serves as a recognition site for a bacteriophage RNA polymerase which converts the DNA sequences into RNA. Suitable RNA polymerases are those from the bacteriophages T7, T3 and SP6. Other suitable types of vectors include cosmids, phage vectors and the like. Viral vectors from mammalian cells can be used if eukaryotic cells are used as hosts.

The plasmids are then further modified to include an insertion element. For example, the MDV DNA insert can be modified to include an insertion element in MDV Mlu I #61 in the plasmids as follows. The synthesized insertion elements are made double stranded for insertion into the plasmid. More particularly, they can be annealed with the corresponding primer oligonucleotide and extended with a DNA polymerase such as Klenow, TAQ and others to produce double stranded DNA molecules. The double stranded molecules are then cut with Mlu I and Nhe I enzymes to produce large DNA fragments containing Mlu I sticky ends 5' and Nhe I sticky ends 3' to the functional nucleotide sequence. These large fragments comprise a insertion element and can be isolated on a polyacrylamide gel.

The fragments are then ligated into Mlu I #61 MDV plasmid DNA which has been cut with Mlu I and Nhe I and gel purified to remove the resulting small fragments. The ligated plasmids now comprise an amplifiable nucleic acid of the invention. The reformed plasmids are transformed into host cells such as *E. coli* to produce a library. The cells are then plated on selective LB plates. Each resulting colony of cells represents a member of the library. Typically, about 100,000 colonies are produced in a library. The various steps and materials used in constructing the libraries are well known and readily available to those skilled in the art.

This strategy has been used to generate insertion elements and libraries of amplifiable nucleic acids of the invention. However, the strategy is not without certain disadvantages. For example, the strategy utilizes relatively long synthetic oligonucleotides which are generally costly and time-consuming to make and are often made with poor overall yields. Where long functional nucleotide sequences and/or spacer elements are necessary for evaluation, it may be difficult to synthesize the correspondingly long insertion elements in sufficient amount for practical use. Thus, the strategy is more readily applicable for use with shorter insertion elements and shorter or fewer spacer elements. It is noted, however, that supplementary strategies can be developed for limiting the disadvantages resulting from overall oligonucleotide size. For example, economies can be gained by synthesizing smaller oligomeric pieces which are then ligated to form a larger, complete oligonucleotide.

The strategy also includes numerous additional steps in the construction of libraries and the corresponding additional expense of time. Finally, care must be taken that the functional nucleotide sequence does not include a restriction site for the enzymes Mlu I and Nhe I or such other enzymes as are used in the construction of the library.

B. A second method for making a library of amplifiable nucleic acids is illustrated schematically in FIG. 3. This method forms a vector library comprising the MDV DNA, a utility sequence and random spacer elements. The utility sequences are thereafter replaced by the functional nucleotide sequence. Although the method illustrates the preparation of Mlu I #61 MDV and two flanking spacer elements, the method is readily adaptable for use with other substrates and other spacer element combinations.

In this method, a DNA oligonucleotide is constructed to include (1) a junk sequence; (2) the Mlu I recognition site; (3) a first spacer element of random nucleotides; (4) a utility sequence of nucleotides; (5) a second spacer element; (6) the nucleotide sequence AGT CAC GG (Seq. ID #2) as before; (7) the Nhe I recognition sequence; and (8) a primer binding site.

The utility sequence is designed to contain restriction sites which permit cleavage as close as possible to the spacer elements. For example, two Bsm I sites can be included near the ends of the sequence. Additionally, the utility sequence can include a site such as an Eco RV site to permit reduction of background recombinants which would otherwise arise from self-ligation of the vector DNA. A library of such oligonucleotides can be made as before using conventional techniques and commercially available nucleic acid synthesizers.

The library of oligonucleotides is processed as in the first method so that double stranded DNAs are produced and then cut with appropriate restriction enzymes, e.g., Mlu I and Nhe I. The resulting fragments are then ligated into Mlu I #61 plasmid DNA. The plasmids are then transformed into a suitable host, e.g., E. coli, forming a base plasmid library comprising the MDV DNA, the utility sequence and flanking spacer elements.

A functional nucleotide sequence is then constructed in double stranded form for insertion into each element of the base library. This can be done, for example, by annealing two complementary synthetic DNA oligonucleotides with appropriate ends. If Mu I #61 plasmids are used as described, the plasmids are then restricted with appropriate enzymes such as Bsm I and Eco RV and then gel purified to remove the resulting small fragments. The double stranded constructs of the functional nucleotide sequences are then ligated into the plasmids forming an amplifiable nucleic acid in the plasmids. The reformed plasmids are then transformed into suitable hosts, e.g., *E. coli*, which are then plated and grown as in method A.

This method B permits libraries to be made more rapidly than method A because the base library can be made independent of the functional nucleotide sequence. Thus, the method is also amenable to the use of longer functional nucleotide sequences. Moreover, the functional nucleotide sequence can be cloned easily and the libraries constructed without concern as to any restriction sites which might be contained within the functional nucleotide sequence.

As was the case with method A described above, the base library should include as many members as is practicable. However, the number of the library members evaluated will still be limited by the time required to construct and evaluate the resulting amplifiable nucleic acids.

This method also has some potential disadvantages. For example, the libraries are produced such that the spacer elements can be separated from the functional nucleotide sequence by a number of nucleotides. When the utility sequence includes the two Bsm I sites suggested above, a spacer element on the 5' side of the functional nucleotide sequence is separated from the functional nucleotide sequence by AG. Similarly, a spacer element on the 3' side is separated from the functional nucleotide sequence by CA. Additionally, the economies noted above are reduced somewhat if spacer elements of varying length are to be evaluated. Then, various base libraries must be made and included in the evaluation, expanding the work involved in the evaluation..

Evaluation of Library Members

The libraries of amplifiable nucleic acids are then evaluated to identify those with excellent replication properties. The libraries can be evaluated applying appropriate conditions for particular selected properties such as replication sensitivity, kinetics, reproducibility and the like. The libraries can also be evaluated for all of these properties collectively. Evaluation is simply tailored to the selected properties of interest and is readily performed by those in the art.

Libraries of amplifiable nucleic acids prepared by methods A and B above can be evaluated in many ways. Typically, individual library members are evaluated as follows. A DNA sample from a cell colony of the library member to be tested is restricted by an appropriate restriction enzyme. When the sample element comprises a Mlu I #61 plasmid as described above, the restriction enzyme is Sma I. T7 RNA polymerase is used to transcribe the DNA construct of the amplifiable nucleic acid into RNA. The RNA is then labelled, e.g., with $^{32}P$-labeled uridine triphosphate (UTP), to permit quantitation of the RNA produced. The amount of RNA produced can be determined by measuring the amount of $^{32}P$-UTP incorporated into the RNA. Thereafter, the RNA transcript is replicated with the appropriate enzyme, e.g., Qβ replicase, under the conditions to be employed in the intended application of the transcript. Those transcripts which replicate with acceptable properties are identified.

For example, the transcripts can be replicated with Qβ replicase in the presence of the intercalating dye propidium iodide and the time required to produce a positive fluorescent response measured. More particularly, replication reactions can be initiated with serial dilutions of molecules of a transcript being evaluated. The transcripts are then evaluated for replication sensitivity and time to produce a detectable signal.

Such replication experiments should take place at about 37° C.±0.25° C. The samples can be excited at 510 nm and read at 610 nm approximately every 40 sec. for a period of 45 minutes. The output fluorescence can then be analyzed numerically for the time of response. The response time can be taken as the intersection of the fluorescent response with the baseline generated prior to the response. The interesection can be determined more precisely using third order polynomials to fit the fluorescent response. A response time so determined is a quantifiable determination of the presence of sample transcript because it is inversely proportional to the log of the number of transcript molecules present in the sample. Cahill et al., Clin. Chem. 37:1482–1488, 1991. Upon identification of an RNA transcript with desirable replication properties, large amounts of template DNA can be made from the original culture.

Those skilled in the art will also appreciate that such evaluations can be applied preliminarily to pools of more than one library member. For example, pools comprising hundreds or thousands of members can be processed as described above. In the event a pool is found to include one or more useful amplifiable nucleic acids of the invention, the pool can be subdivided into increasingly smaller pools to identify the most exceptional amplifiable nucleic acids within the original pool of library members. This method is particularly advantageous in those instances where a large numbers of library members are to be tested and the most superior amplifiable nucleic acids are desired.

For use in a diagnostic assay, amplifiable nucleic acids of the invention should provide excellent replication properties including (1) sensitivity, i.e., it is desirable that a single molecule be able to initiate a detectable replication reaction (2) reproducibility, i.e., replication should proceed in a well defined and consistant manner irrespective of the number of molecules used to initiate the replication reaction; (3) rapid, i.e., detection should be permitted in about 30 min. irrespective of the number of molecules used to initiate the replication reaction; (4) linearity, i.e., response times should be linear relative to the logarithm of the number of molecules used to initiate the replication reaction; and (5) maintain all of these properties when bound to an assay target. The methods described here have been used to make numerous libraries and identify numerous amplifiable nucleic acids of the invention with excellent replication properties for various functional nucleotide sequences.

EXAMPLES

Example 1

This example demonstrates the preparation, identification and replication properties of useful insertion elements, amplifiable nucleic acids and a library of the invention. The amplifiable nucleic acids and library were made using method A as described above.

Materials

As used herein, restriction enzymes, the Klenow fragment of *E. coli* DNA polymerase I and T4 DNA ligase were purchased from New England BioLabs. RNA molecules were transcribed in vitro using the Riboprobe Gemini II transcription system purchased from Promega Corp. Ribonucleoside 5'-triphosphates were supplied by Pharmacia, deoxyribonucleotide 5'-triphosphates were obtained from Boehringer Mannheim and $^{32}$P-UTP was purchased from DuPont NEN. Propidium iodide and ampicillin were purchased from Sigma Chemical. Competent *E. coli* DH5α cells were used for all transformations and were bought from Gibco BRL. Oligonucleotides were made on an Advanced Biosystems, Inc. synthesizer and purified on denaturing polyacrylamide gels before use. Recombinant Qβ replicase was expressed from a lambda pL promoter using the expression vector pPL-Lambda in *E. coli* N99cI+cells (both from Pharmacia).

Library Construction

Amplifiable nucleic acids and library constructions were made using MDV cDNA which was produced as follows. Two synthetic oligonucleotides were made representing the plus and minus strands of MDV as reported by Mills et al., Science 180, 916–927 (1973). The strands were made to partially overlap as follows. The plus strand oligonucleotide comprised sequences (from 5–to 3') for a Hind III site, T7 promoter, and nucleotides 1 to 113 of the plus strand of MDV. The minus strand oligonucleotide comprised sequences from the 5' end for an Eco RI site, Sma I site and the sequence complementary to nucleotides 102 to 222 of the plus strand of MDV. The oligonucleotides were annealed, extended with the Klenow fragment of *E. coli* DNA polymerase I, cut with Hind Imi and Eco RI and cloned into pUC19 plasmid DNA. The resulting MDV cDNA substituted U for C at bases 117 and 136 and A for G at base 137 of the plus strand of MDV. Thereafter, the nucleotides from bases 9 to 71 were replaced by annealed synthetic oligonucleotides to introduce the nucleotides CGT after nucleotide 63 thereby creating a unique Mlu I site (ACG CGT, Seq. ID #1). This DNA was restricted with Mlu I and Nhe I and used as the vector in the cloning procedures described below.

The library was constructed as follows. Insertion elements were synthesized with the following basic features 5' ACG CGT $(N)_{10}$ -|FNS|-$(N)_{10}$ AGT CAC GGG CTA GC -|Primer Site| 3' where N is any of the four deoxyribonucleotides chosen at random during synthesis. The functional nucleotide sequence (FNS) was AGG CCT TTA CCC CAC CAA CTA GCT GAT ATC ACA TA (Seq. ID #7). This sequence of nucleotides binds to the 16S rRNA of *Chlamydia trachomatis*. The primer site was CCC TAT AGT GAG TCG TAT TAG CAA GCT (Seq. ID #8). The first twenty nucleotides of this sequence are complementary to the T7 promoter primer which was used to form the double stranded DNA. Next, a primer for the T7 promoter primer was annealed to the primer site and extended at 37° C. in 9 mM Tris pH 7.5, 90 mM NaCl, 15 mM $MgC_2$, 1 mM dithiothreitol (DTT), 500 μM nucleoside triphosphates (dGTP, dATP, dTTP, dCTP) and 0.1 U/μl of the Klenow fragment of DNA polymerase I.

Next, the double-stranded DNA product was restricted with Mlu I and Nhe I, gel purified, and ligated into the MDV cDNA vector described above. Finally, 1/10 (about 2 μl) of the ligated material was transformed into DH5α *E. coli* cells. The cells were plated onto LB plates with 100 μg/ml ampicillin for screening.

Replication Assays

Thirty-six individual members of the library were screened as follows. 10 ml of bacterial culture was grown overnight in LB media and 100 μg/ml ampicillin. Plasmid DNA was isolated from 1.5 ml of culture, restricted with Sma I and transcribed into RNA using T7 RNA polymerase in the presence of a trace amount of $^{32}$P-UTP. RNA transcripts were quantitated by measuring the percent of incorporation of the $^{32}$P-UTP as measured by retention of radioactivity on DE81 ion exchange filters (Whatman) using washes of 0.5M $Na_2HPO_4$, pH 7.5.

The RNA molecules were examined for size and integrity by denaturing polyacrylamide gel electrophoresis. The RNA substrates were then diluted and replicated in duplicate with Qβ replicase which was purified free of endogenous MDV RNA as described in U.S. Pat. No. 5,141,857 which is incorporated herein by reference.

Those RNAs showing good replication sensitivity and kinetics were analyzed further by preparing CsCl-banded DNA from 500 ml bacterial cultures, transcribing these with T7 RNA polymerase as described previously, and conducting additional amplification reactions with Qβ replicase.

The DNA sequence of individual spacer elements was determined using the Sequenase Version 1.0 kit (United States Biochemical ) and the T7 promotor primer which hybridizes to the T7 promoter sequence.

RNA substrates obtained as described were diluted in 50 mM Tris (pH 8.0), 1 mM EDTA and 0.5% NP40 to concentrations of $1\times10^n$ per 50 μl where the superscript n varied from 0 to 10. 50 μl samples of these dilutions were added to 50 μl of ice cold 220 mM Tris pH 7.8, 34 mM $MgCl_2$, 0.8 mM GTP, ATP, CTP and UTP, 2.0 μg/ml propidium iodide and 25% glycerol containing approximately 110 μg/ml Qβ replicase.

The replication reactions were initiated by mixing these materials together and bringing the temperature of the reaction mixture to 37° C.±0.25° C. where it was held for the duration of the replication. The materials were brought to 37° C. in about 40 sec. The reaction mixtures were measured for fluorescence by stimulating (510 nm) and measuring (610 nm) every 40 seconds for 45 minutes. The output fluorescence was analyzed numerically to determine the time of response. The response time was taken as the intersection of the fluorescent response with the baseline generated prior to the response. Third order polynomials were used to fit the response curve and determine the intersection. The fluorometer used is able to detect fluorescence generated from about $5*10^{11}$ molecules. The replication sensitivity or limit of detection is determined as the smallest number of substrate molecules sufficient to produce a response time.

These assays also permit determination of kinetic information such as the time for replication of each substrate. The response time is a function of the number of substrate molecules used to start the replication and the time required for Qβ replicase to synthesize a complementary strand. The time required to synthesize a complementary strand is referred to as the doubling time and can be approximated from the formula:

$$DT=(RT-0.7) (\log 2) / \log (5*10^{11}/N)$$

where DT is the doubling time,

RT is the response time in minutes,

N is the number of substrate molecules at the start of the reaction, and $5*10^{11}$ is approximately the number of substrate molecules present at detection.

About 40 sec. or 0.7 min. is subtracted from the response time to account for the time the reaction mixture is being brought to 37° C. Those skilled in the art will also understand that doubling times are sensitive to reaction conditions and that doubling times are meaningfully compared only for identical reaction conditions.

Results

Flanking spacer elements were found to have a pronounced effect upon the replication properties of RNA substrates prepared herein. This is illustrated in Tables 1 and 2 below. Table 1 identifies the spacer elements incorporated in six of the substrates.

TABLE 1

Spacer Elements for 6 RNA Amplifiable Nucleic Acids

| RNA | 5' Spacer Element | 3' Spacer Element |
|---|---|---|
| C7 | TACTTATCTG (Seq. ID #9) | CTGAGTGTAG (Seq. ID #10) |
| C4 | TATATAAGGT (Seq. ID #11) | GTTCTCGTGT (Seq. ID #12) |
| C22 | GGGGTGGGCA (Seq. ID #13) | TGTGTAATAT (Seq. ID #14) |
| C6 | AACGTAACTA (Seq. ID #15) | CATTTTACGA (Seq. ID #16) |
| C11 | CTGTACTAAT (Seq. ID #17) | ATTACGTGGG (Seq. ID #18) |
| C8 | GGATGTCAGG (Seq. ID #19) | CAGGGGTTGT (Seq. ID #20) |

Table 2 provides sensitivity and kinetic information for replication of the six RNA substrates.

TABLE 2

Replication Properties of 6 RNA Amplifiable Nucleic Acids

| RNA | Replication Limit (# of molecules) | RNA Doubling Time (Seconds) |
|---|---|---|
| C7 | 1 | 45.8 |
| C4 | 1 | 35.9 |
| C22 | 1 | 21.3 |
| C6 | 100 | 45.3 |
| C11 | 1000 | 46.6 |
| C8 | 10,000 | 61.2 |

Table 2 demonstrates that spacer elements can have a pronounced effect on the sensitivity and kinetics of replication of amplifiable nucleic acids of the invention. However, as shown in the table, the RNA substrates C7, C4 and C22 permitted detectable replication of one substrate molecule. In contrast, the RNA substrate C8 permitted detectable replication of only 10,000 molecules or a difference of four orders of magnitude in sensitivity. Table 2 also shows that the doubling time of C22 was about 21 sec. or about one third of the 61 sec. doubling time for C8.

The RNA substrates C7, C4 and C22 demonstrate excellent replication sensitivity. The RNA substrate C22 also demonstrates excellent replication kinetics and can be used directly as a replicable detector probe with propidium iodide in sandwich hybridization assays for *Chlamydia trachomatis*.

Example 2

This Example demonstrates the detection of *Chlamydia trachomatis* using an amplifiable nucleic acid of the invention in two assay formats. The assay formats are nominally identified as Dual Capture and Reversible Target Capture (RTC) assays. The Dual Capture assay used two capture probes. These were the B-3018 and dA-781 capture probes. The RTC assay used only the dA-781 capture probe. Both assays used the amplifiable nucleic acid C29 as a detector probe.

Materials

Paramagnetic particles derivatized with oligo $dT_{14}$ were prepared for use in this Example as follows. Sub-micron ferric oxide particles (Advanced Magnetics, Inc., Cambridge, Mass.) were derivatized with $dT_{14}$ oligomers using the method described by Morrissey, Anal. Biochem., 181:345–349 (1989). The beads were blocked for 4 hrs. at 65° C. in Bead Blocking Buffer [100 mM Tris 4.9% BSA (Bovine Serum Albumin, Sigma Fraction 5, 0.5% Sarkosyl (Sigma), 10 mM EDTA, 0.05% Bronopol (Inolex, Philadelphia, PA), 0.01 % antifoam (Dow-Corning FG-10], ph 7.8. The final suspension of particles was 0.25%(W/V) solids with a binding capacity of 300 pmol (deoxyadenylate) $dA_{50}$per mg. Just before use, particles were separated from the buffer and made up to 0.045% in fresh Bead Blocking Buffer and Bead Blocking Buffer plus 4M guanidine hydrochloride (GuHCl).

Paramagnetic particles derivatized with streptavidin were obtained from Promega (Madison, Wis.). Purified 16S rRNA from *Chlamydia trachomatis* was used as the target in this example. The 16S rRNA was purified using conventional techniques.

Certain nucleic acid sequences are incorporated into the probes used in this example. These are:

| Sequence Ref. No. | Sequence (5'-3') |
|---|---|
| 3018 (Sequence ID #21) | cCTTTAACGTTACTCGGATGCCCAAA |
| 781 (Sequence ID #22) | CTTTAACGTTACTCGGATGCCCAAATATCGCCACAT |
| C29 (Sequence ID #23) | GGGGACCCCCCCGGAAGGGGGGGGACGAG-GUGCGGGCACCUCGUACGGGAGUUCGAC-CGUGACGCGUCGUCGAGUUGAGGCCUUU-ACCCCACCAACUAGCUGAUAUCAC-AUACUGAAUCUUUAGTCACGGGCU-AGCGCUUUCGCGCUCUCCCAGGUGACGC-CUCGUGAAGAGGCGUGACCUUCGUGCGU-UUCGGUAACGCACGAGAACCGCCACGCU-GCUUCGCAGCGUGGCCCCUUCGCGCAGC-CCGCUGCGCGAGGUGACCCCCCGAAGGG-GGGUUCCC |

The nucleic acid sequences 3018 and 781 were made using conventional beta-cyanoethyl phosphoramidite chemistry and conventional nucleic acid synthesizer equipment such as the 380-B Synthesizer from Applied Biosystems, Foster City, Calif. The sequences were modified for use as capture and detector probes as follows.

The sequence 3018 (Sequence ID # 21) was biotinylated to form probe B-3018 by first modifying the 5' end of sequence 3018 (sequence ID # 21) to contain a primary amine. This was accomplished by addition of an aminopropyl-modified cytidine phosphoramidite. Deprotection of the phosphates and nucleotide bases was accomplished by standard methods. The crude oligonucleotide mixtures were purified by reverse phase HPLC. The amino modified oligonucleotide was labeled with biotin using the Fluo Reporter Biotin Labeling Kit, F-2610 from Molecular Probes, Inc.

The sequence 781 (Sequence ID # 22) was tailed with about 150 deoxyadenylate residues at the 3' end of each sequence to form probe dA-781. This was accomplished by incubation with terminal deoxynucleotidyl transferase (Life Sciences, Inc.) following the method of Nelson et al. Methods in Enzymology, 68: 41–47, 1979.

The RNA C29 (Seq. ID # 23) was used as the detector probe in all assays without further modification. C29 (Seq. ID # 23) is an amplifiable nucleic acid of the invention. It includes the RNA transcript of the same functional nucleotide sequence included in the amplifiable RNAs of Example 1. The functional nucleotide sequence is flanked by two spacer elements. The 5' and 3' spacer elements are respectively CGUCGAGUUG (Seq. ID # 24) and CUGAAUCUUU (Seq. ID # 25). These are underlined in the sequence for C29 printed above. C29 was identified as an excellent amplifiable nucleic acid using method A described herein.

The C29 (Seq. ID # 23) used herein was made from a DNA sequence complementary to C29 RNA. The DNA was prepared by conventional methods and cloned into a T7 transcription vector. C29 was transcribed from the cloned DNA using a T7 RNA polymerase kit from Promega.

The assays were performed as follows. Two solutions were prepared: Solution 1 was made up to comprise 700 microliters of $1.4 * 10^6$ purified Chlamydia target molecules, 70 ng B-3018 capture probe, $1.4 * 10^{12}$ molecules of C29 detector probe in 4M guanidine hydrochloride (GuHCl), 125 mM Tris pH 7.8 and 16 mM EDTA.
Solution 2 was made up to comprise 700 microliters of $1.4 * 10^6$ purified Chlamydia target molecules, 70 ng dA-781 capture probe, $1.4 * 10^{12}$ molecules of C29 detector probe in 4M GuHCl, 125 mM Tris pH 7.8, 16 mM EDTA.

Twenty-four of the wells of an 8(A–H)×12(1–12) 96 well rack for 1.5 ml polypropylene tubes (Micronics, Flow Laboratories, McLean, Va.) were used. Fifty microliter aliquots of solutions 1–2 were added to twenty-four of the tubes as follows:

50 µl ($10^5$ target molecules plus probes) Solution 1 was added to tubes A-B 1–6.

50 µl ($10^5$ target molecules plus probes) Solution 2 was added to tubes A-B 7–12.

The content of the rack can be represented schematically as follows:

Rack setup:

| | ←Dual Capture→ | | | | | | ←Standard RTC→ | | | | |
|---|---|---|---|---|---|---|---|---|---|---|---|
| | 1 | 2 | 3 | 4 | 5 | 6 | 7 | 8 | 9 | 10 | 11 | 12 |
| A | ←$10^5$ target + B-3018 + C29→ | | | | | | ←$10^5$ target + dA-781 + C29→ | | | | | |
| B | ←$10^5$ target + B-3018 + C29→ | | | | | | ←$10^5$ target + dA-781 + C29→ | | | | | |

All tubes were incubated for 30 min. at 37° C. to allow the Chlamydia target to hybridize to capture probe and detector probe. Following incubation, a 350µl suspension of 0.023% streptavidin derivatized particles in Bead Blocking Buffer [4% BSA (Bovine Serum Albumin, Sigma Fraction 5), 0.5% Sarkosyl, 100 mM Tris, 20mM EDTA, 0.01% antifoam], pH 8.0 was added to each of tubes A-B 1–6. A 100µl suspension of 0.045% $dT_{14}$ derivatized particles in Bead Blocking Buffer containing 4M GuHCl was added to each of tubes A-B 7–12. After mixing on a platform vortex, the tubes were incubated at 37° C. for 5 min. to capture the ternary capture probe:target:detector probe complexes. The particles and captured ternary complexes were collected at the sides of the tubes using a magnetic separations deviced as described in U.S. Pat. No. 4,988,618 to Li et al., which is incorporated herein by reference. The supernatants were aspirated away.

Next, the particles were washed to remove detector probe unbound to the target. Two hundred microliters of Wash Buffer [300 mM NaCl, 0.5% Sarkosyl], 100 mM Tris, 20 mM EDTA, 0.5% BSA, 0.1% antifoam], pH 8.1 was added to each tube. The tubes were mixed and incubated at 37° C. for 2 min. The particles and captured ternary complexes were collected at the sides of the tubes as described above. The supernatants were aspirated away. The particles were washed twice more in the same manner.

Next, 160 µl of Guanidine Thiocyanate (GuSCN) Buffer [2.5M GuSCN, 100 mM Tris, 10 mM EDTA, 0.5% Sarkosyl, and 0.5% BSA], pH 7.8 was added to each tube. After mixing, the tubes were incubated at 37° C. for 5 min. This resulted in release of the target:detector probe segment of the ternary complex in tubes A-B 1–6, and release of the capture probe:target:detector probe ternary complex in tubes A–B 7–12. The B-3018 capture probe remains bound to the streptavidin particles in tubes A–B 1–6. After 5 min. the particles were collected at the sides of the tubes using a magnetic separation device as described above. The supernatants were transferred to clean tubes.

Next, 40 µl of 500 ng/ml dA-781 capture probe in 10 mM Tris, 1 mM EDTA was added to each supernatant of tubes A–B 1–6. Forty microliters of 10 mM Tris and 1 mM EDTA was added to each supernatant of tubes A–B 7–12. The tubes were incubated for 30 min. at 37° C. to allow dA-781 capture probe to hybridize to the target: detector probe segment in tubes A–B 1–6. Three hundred microliters of 0.05% $dT_{14}$ particles in Bead Blocking Buffer was added to all tubes. The ternary complexes were captured on the $dT_{14}$ particles. The particles were collected at the sides of the tubes as described above and the supernatants were aspirated away. The particles were then washed with Wash Buffer as described above to remove detector probe unbound to the target. The supernatant was aspirated away.

Next, the ternary complexes were released from the particles by addition of 100 µl Release Buffer [25 mM NaCl, 100mM Tris, 20 mM EDTA, 0.2% Sarkosyl, 0.05% Bronopol and 0.05% BSA], pH 8.1 as described above. The supernatants with released ternary complexes were transferred to clean tubes.

Next 200 µl of a suspension of 0.045% oligo $dT_{14}$ particles in Buffer A [4% BSA, 4M GuHCl, 100mM Tris, 20 mM EDTA, 0.5% Sarkosyl, and 0.1% antifoam], pH 7.8 was added to each of the released supernatants. The ternary complexes were captured onto the particles as described above. The particles were collected at the sides of the tubes as described above and the supernatants were aspirated away.

The particles were then washed twice in pre-Amp Wash Buffer [300 mM KCl, 50 mM Tris, 1 mM EDTA], pH8.0. The supernatants were aspirated away. Next, 150 µl of Pre-Amp Release Buffer [50 mM Tris, 1 mM EDTA, 0.5% NP-40] was added to each tube. After mixing, the tubes were incubated at 37° C. This resulted in release of the ternary complexes. The particles were separated from the supernatants as described before.

The presence of target was determined by replicating the C29 detector probe with Qβ-replicase in the presence of the intercalating dye propidium iodide and measuring the time required to produce a positive response. More particularly, 100 µl of the supernatant from each tube was added to a 100 µl mixture of 220 mM Tris pH 7.8, 40 mM $MgCl_2$, 1.2 mM each of the nucleotide triphosphates ATP, CTP, GTP and UTP (Pharmacia), 2 µg/ml propidium iodide, 25% glycerol and 110µg/ml of purified Qβ-replicase (specific activity of about 2,000 units/mg). The Qβ-replicase was obtained as described in U.S. Pat. No. 5,141,857 which is incorporated herein by reference. The tubes were capped and kept on ice until ready for measurement.

The tubes were processed simultaneously. Each tube was maintained at 37° C.±0.25° C. Each tube was excited at 510nm and read at 610nm every 40 sec. for a period of 45 min. The output fluorescence was analyzed numerically for response time. The response time was taken as the intersection of the fluorescent response with the baseline. The intersection was determined using third order polynomials to fit the fluorescent response. The baseline was averaged.

Ten of the 12 tubes for the Dual Capture method were measured. All 10 produced a positive response. Eleven of the 12 tubes for the standard RTC method were measured. All 11 produced a positive response. Thus, the example demonstrates both assay formats are able to detect the signal generated by $10^5$ molecules of target 16S rRNA using the C29 detector probe.

Example 3

Table 3 identifies additional RNA insertion elements which are useful in amplifiable nucleic acids of the invention. The insertion elements were identified by constructing libraries as described in methods A and B and evaluating the members of the libraries as described previously. The spacer elements and functional nucleotide sequence of each insertion element are identified. These insertion elements have been incorporated into MDV Mlu I #61 RNA and used as replicable detector probes in sandwich hybridization assays. Table 3 also identifies the test organism and the source of the nucleic acid to which the functional nucleotide sequence is designed to bind. Finally, Table 3 identifies the general method A or B as described in the Detailed Description of the Invention used to construct the library from which each insertion element was found.

TABLE 3

Insertion Elements For Test Organisms

| RNA Insertion Elements | Test Organism(s) | 5' Spacer |
|---|---|---|
| G2 (Seq. ID #26) | *Neisseria gonorrhoeae** (16S rRNA) | GAGAACAAAU |
| F43 (Seq. ID #27) | *Fungemia**[1] (18S rRNA) | AAGGUACCAC |
| B57 (Seq. ID #28) | *Bacteremia***[2] (16S rRNA) | UGAUAUAUUCAG (AG) |
| MC7 (Seq. ID #29) | *Mycobacterium tuberculosis*** (23S rRNA) | GGGCGUGUGA (A) |
| MZ28 (Seq. ID #30) | *Mycobacterium tuberculosis*** (23S rRNA) | CUGUACGGUUUG (AG) |
| PC8 (Seq. ID #31) | Pneumocystis Carinii** (18S rRNA) | GUCAAUGGAGG (AG) |

| RNA Insertion Elements | Functional Nucleotide Sequence | 3' Spacer |
|---|---|---|
| G2 (Seq. ID #26) | CCCAUGCAGCACCUGUGUUACGGCUCCCGAAGGCAG | AGUGUGUUUU |
| F43 (Seq. ID #27) | UGGUGCCCUUCCGUCAAUUUCUUUAAGUUUCAGCCUUGCG | GCCGAUCCGA |
| B57 (Seq. ID #28) | UGGGCCGUGUCUCAGUUCCAGUGGCUGGUCAUUCUC | (A) CAGAUCAUAGAU |

TABLE 3-continued

| Insertion Elements For Test Organisms | | |
|---|---|---|
| MC7 (Seq. ID #29) | GUCCCUGACUCGCAGGCUCAUUCUUCAAAAGGCACG | (CA) UUGUGCCAGAGA |
| MZ28 (Seq. ID #30) | UGUGGGUCGCCCUAUUCAGACUCGCUUUCGCUGCG | (CA) CUCACAGAGCUA |
| PC8 (Seq. ID #31) | UCCUCGUUAAGGGAUUAAAUUGUACUCAUUCCAAUUA | (CA) UUGAGCCUUUAG |

*These insertion elements were identified from a library prepared as described in Method A.
**These insertion elements were identified from a library prepared as described in Method B.
[1]The functional nucleotide sequence binds to the 16S rRNA of most eubacteria under appropriate hybridization conditions.
[2]The functional nucleotide sequence binds the 18S rRNA of most fungi under appropriate hybridization conditions.

---

SEQUENCE LISTING ( 1 ) GENERAL INFORMATION:

( i i i ) NUMBER OF SEQUENCES: 32

( 2 ) INFORMATION FOR SEQ ID NO:1:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:1:

A C G C G T                 6

( 2 ) INFORMATION FOR SEQ ID NO:2:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:2:

A G T C A C G G             8

( 2 ) INFORMATION FOR SEQ ID NO:3:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:3:

G C T A G C                 6

( 2 ) INFORMATION FOR SEQ ID NO:4:

( i ) SEQUENCE CHARACTERISTICS:
        ( A ) LENGTH: 122 base pairs (B) TYPE: nucleic acid
(C) STRANDEDNESS: single
(D) TOPOLOGY: linear (iii) HYPOTHETICAL: NO (iv) ANTI-SENSE: NO (xi) SEQUENCE DESCRIPTION: SEQ ID NO:4:

```
GCTCATCTGA GTCATCCAAG TACGCGTNNN NNNNNNNAGG CCTTTACCCC ACCAACTAGC      60
TGATATCACA TANNNNNNNN NNAGTCACGG GCTAGCCCTA TAGTGAGTCG TATTAGCAAG     120
CT                                                                    122
```

(2) INFORMATION FOR SEQ ID NO:5:

(i) SEQUENCE CHARACTERISTICS:
(A) LENGTH: 132 base pairs
(B) TYPE: nucleic acid
(C) STRANDEDNESS: single
(D) TOPOLOGY: linear (iii) HYPOTHETICAL: NO (iv) ANTI-SENSE: NO (xi) SEQUENCE DESCRIPTION: SEQ ID NO:5:

```
GCTCATCTGA GTCATCCAAG TACGCGTNNN NNNNNNNCTG CTGCCTCCCG TAGGAGTTTG      60
GGCCGTGTCT CAGTTCCAGT GTNNNNNNNN NNAGTCACGG GCTAGCCCTA TAGTGAGTCG     120
TATTAGCAAG CT                                                         132
```

(2) INFORMATION FOR SEQ ID NO:6:

(i) SEQUENCE CHARACTERISTICS:
(A) LENGTH: 127 base pairs
(B) TYPE: nucleic acid
(C) STRANDEDNESS: single
(D) TOPOLOGY: linear (iii) HYPOTHETICAL: NO (iv) ANTI-SENSE: NO (xi) SEQUENCE DESCRIPTION: SEQ ID NO:6:

```
GCTCATCTGA GTCATCCAAG TACGCGTNNN NNNNNNNTGG TGCCCTTCCG TCAATTTCTT      60
TAAGTTTCAG CCTTGCGNNN NNNNNNNAGT CACGGGCTAG CCCTATAGTG AGTCGTATTA     120
GCAAGCT                                                               127
```

(2) INFORMATION FOR SEQ ID NO:7:

(i) SEQUENCE CHARACTERISTICS:
(A) LENGTH: 35 base pairs
(B) TYPE: nucleic acid
(C) STRANDEDNESS: single
(D) TOPOLOGY: linear (iii) HYPOTHETICAL: NO (iv) ANTI-SENSE: NO (xi) SEQUENCE DESCRIPTION: SEQ ID NO:7:

```
AGGCCTTTAC CCCACCAACT AGCTGATATC ACATA                                 35
```

(2) INFORMATION FOR SEQ ID NO:8:

(i) SEQUENCE CHARACTERISTICS:
(A) LENGTH: 27 base pairs (B) TYPE: nucleic acid
(C) STRANDEDNESS: single
(D) TOPOLOGY: linear (i i i) HYPOTHETICAL: NO (i v) ANTI-SENSE: NO (x i) SEQUENCE DESCRIPTION: SEQ ID NO:8:

CCCTATAGTG AGTCGTATTA GCAAGCT 27

(2) INFORMATION FOR SEQ ID NO:9:

(i) SEQUENCE CHARACTERISTICS:
(A) LENGTH: 10 base pairs
(B) TYPE: nucleic acid
(C) STRANDEDNESS: single
(D) TOPOLOGY: linear (i i i) HYPOTHETICAL: NO (i v) ANTI-SENSE: NO (x i) SEQUENCE DESCRIPTION: SEQ ID NO:9:

TACTTATCTG 10

(2) INFORMATION FOR SEQ ID NO:10:

(i) SEQUENCE CHARACTERISTICS:
(A) LENGTH: 10 base pairs
(B) TYPE: nucleic acid
(C) STRANDEDNESS: single
(D) TOPOLOGY: linear (i i i) HYPOTHETICAL: NO (i v) ANTI-SENSE: NO (x i) SEQUENCE DESCRIPTION: SEQ ID NO:10:

CTGAGTGTAG 10

(2) INFORMATION FOR SEQ ID NO:11:

(i) SEQUENCE CHARACTERISTICS:
(A) LENGTH: 10 base pairs
(B) TYPE: nucleic acid
(C) STRANDEDNESS: single
(D) TOPOLOGY: linear (i i i) HYPOTHETICAL: NO (i v) ANTI-SENSE: NO (x i) SEQUENCE DESCRIPTION: SEQ ID NO:11:

TATATAAGGT 10

(2) INFORMATION FOR SEQ ID NO:12:

(i) SEQUENCE CHARACTERISTICS:
(A) LENGTH: 10 base pairs
(B) TYPE: nucleic acid
(C) STRANDEDNESS: single
(D) TOPOLOGY: linear (i i i) HYPOTHETICAL: NO (i v) ANTI-SENSE: NO (x i) SEQUENCE DESCRIPTION: SEQ ID NO:12:

GTTCTCGTGT 10

( 2 ) INFORMATION FOR SEQ ID NO:13:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:13:

GGGGTGGGCA    10

( 2 ) INFORMATION FOR SEQ ID NO:14:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:14:

TGTGTAATAT    10

( 2 ) INFORMATION FOR SEQ ID NO:15:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:15:

AACGTAACTA    10

( 2 ) INFORMATION FOR SEQ ID NO:16:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:16:

CATTTTACGA    10

( 2 ) INFORMATION FOR SEQ ID NO:17:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:17:

CTGTACTAAT 10

( 2 ) INFORMATION FOR SEQ ID NO:18:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:18:

ATTACGTGGG 10

( 2 ) INFORMATION FOR SEQ ID NO:19:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:19:

GGATGTCAGG 10

( 2 ) INFORMATION FOR SEQ ID NO:20:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:20:

CAGGGGTTGT 10

( 2 ) INFORMATION FOR SEQ ID NO:21:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:21:

CCTTTAACGT TACTCGGATG CCCAAA 26

( 2 ) INFORMATION FOR SEQ ID NO:22:

( i ) SEQUENCE CHARACTERISTICS:
        ( A ) LENGTH: 36 base pairs
        ( B ) TYPE: nucleic acid
        ( C ) STRANDEDNESS: single (D) TOPOLOGY: linear (iii) HYPOTHETICAL: NO (iv) ANTI-SENSE: NO (xi) SEQUENCE DESCRIPTION: SEQ ID NO:22:

CTTTAACGTT ACTCGGATGC CCAAATATCG CCACAT    36

(2) INFORMATION FOR SEQ ID NO:23:

(i) SEQUENCE CHARACTERISTICS:
        (A) LENGTH: 280 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:23:

GGGGACCCCC CCGGAAGGGG GGGACGAGGU GCGGGCACCU CGUACGGGAG UUCGACCGUG    60

ACGCGUCGUC GAGUUGAGGC CUUUACCCCA CCAACUAGCU GAUAUCACAU ACUGAAUCUU   120

UAGTCACGGG CUAGCGCUUU CGCGCUCUCC CAGGUGACGC CUCGUGAAGA GGCGUGACCU   180

UCGUGCGUUU CGGUAACGCA CGAGAACGC CACGCUGCUU CGCAGCGUGG CCCCUUCGCG   240

CAGCCCGCUG CGCGAGGUGA CCCCCCGAAG GGGGGUUCCC                         280

(2) INFORMATION FOR SEQ ID NO:24:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:24:

CGUCGAGUUG    10

(2) INFORMATION FOR SEQ ID NO:25:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:25:

CUGAAUCUUU    10

(2) INFORMATION FOR SEQ ID NO:26:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (iii) HYPOTHETICAL: NO ( i v ) ANTI-SENSE: NO ( x i ) SEQUENCE DESCRIPTION: SEQ ID NO:26:

GAGAACAAAU CCCAUGCAGC ACCUGUGUUA CGGCUCCCGA AGGCAGAGUG UGUUUU  56

( 2 ) INFORMATION FOR SEQ ID NO:27:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:27:

AAGGUACCAC UGGUGCCCUU CCGUCAAUUU CUUUAAGUUU CAGCCUUGCG GCCGAUCCGA  60

( 2 ) INFORMATION FOR SEQ ID NO:28:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:28:

AAGGUACCAC UGGUGCCCUU CCGUCAAUUU CUUUAAGUUU CAGCCUUGCG GCCGAUCCGA  60

( 2 ) INFORMATION FOR SEQ ID NO:29:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:29:

UGAUAUAUUC AGAGUGGGCC GUGUCUCAGU UCCAGUGGCU GGUCAUUCUC ACAGAUCAUA  60

GAU  63

( 2 ) INFORMATION FOR SEQ ID NO:30:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:30:

GGGCGUGUGA AGUCCCUGAC UCGCAGGCUC AUUCUUCAAA AGGCACGCAU UGUGCCAGAG  60

A  61

( 2 ) INFORMATION FOR SEQ ID NO:31:

-continued (i) SEQUENCE CHARACTERISTICS:
  (A) LENGTH: 63 base pairs
  (B) TYPE: nucleic acid
  (C) STRANDEDNESS: single
  (D) TOPOLOGY: linear (iii) HYPOTHETICAL: NO (iv) ANTI-SENSE: NO (xi) SEQUENCE DESCRIPTION: SEQ ID NO:31:

CUGUACGGUU UGAGUGUGGG UCGCCCUAUU CAGACUCGCU UUCGCUGCGC ACUCACAGAG    60

CUA    63

(2) INFORMATION FOR SEQ ID NO:32:

(i) SEQUENCE CHARACTERISTICS:
  (A) LENGTH: 64 base pairs
  (B) TYPE: nucleic acid
  (C) STRANDEDNESS: single
  (D) TOPOLOGY: linear (iii) HYPOTHETICAL: NO (iv) ANTI-SENSE: NO (xi) SEQUENCE DESCRIPTION: SEQ ID NO:32:

GUCAAUGGAG GAGUCCUCGU UAAGGGAUUA AAUUGUACUC AUUCCAAUUA CAUUGAGCCU    60

UUAG    64

The foregoing are but examples of the insertion elements, amplifiable nucleic acids and libraries of the invention. Those skilled in the art will recognize that additional embodiments of the invention are readily available.

Accordingly, that which is claimed is:

1. An amplifiable nucleic acid comprising a replicable nucleic acid substrate, a functional nucleotide sequence and at least one spacer element comprising a sequence of random nucleotide flanking the functional nucleotide sequence and wherein the functional nucleotide sequence and at least one flanking spacer elements are internal to the replicable nucleic acid substrate, and the functional nucleotide sequence binds to a nucleotide sequence of a target polynucleotide under hybridization conditions.

2. The amplifiable nucleic acid of claim 1 wherein the functional nucleotide sequence is flanked on each of its 3' and 5' sides by a spacer element.

3. The amplifiable nucleic acid of claim 2 wherein each of the spacer elements consists of from 2 to 25 nucleotides.

4. The amplifiable nucleic acid of claim 2 wherein the replicable nucleic acid substrate is a substrate for Qβ replicase.

5. The amplifiable nucleic acid of claim 4 wherein the replicable nucleic acid substrate is an MDV RNA.

6. The amplifiable nucleic acid of claim 1 wherein the spacer elements consist of from 8 to 14 nucleotides and the replicable nucleic acid substrate is a substrate for Qβ replicase.

7. The amplifiable nucleic acid of claim 1 wherein the functional nucleic acid is flanked on its 3' side by a spacer element consisting of from 2 to 25 nucleotides and the replicable nucleic acid substrate is a substrate for Qβ replicase.

8. The amplifiable nucleic acid of claim 7 wherein the spacer element consists of from 8 to 14 nucleotides and the replicable nucleic acid substrate is an MDV RNA.

9. The amplifiable nucleic acid of claim 1 wherein the functional nucleic acid is flanked on its 5' side by a spacer element consisting of from 2 to 25 nucleotides and the replicable nucleic acid substrate is a substrate for Qβ replicase.

10. The amplifiable nucleic acid of claim 9 wherein the spacer element consists of from 8 to 14 nucleotides and the replicable nucleic acid substrate is an MDV RNA.

11. A library of amplifiable nucleic acids wherein each amplifiable nucleic acid of the library comprises a replicable nucleic acid substrate, a functional nucleotide sequence and at least one spacer element comprising a sequence of random nucleotides flanking the functional nucleotide sequence and wherein the functional nucleotide sequence and at least one flanking spacer elements are internal to the replicable nucleic acid substrate, and the functional nucleotide sequence binds to a nucleotide sequence of a target polynucleotide under hybridization conditions.

12. The library of amplifiable nucleic acids of claim 11 wherein the functional nucleotide sequence of each amplifiable nucleic acid is flanked on each of its 3' and 5' sides by a spacer element.

13. The library of amplifiable nucleic acids of claim 12 wherein the replicable nucleic acid substrate of each amplifiable nucleic acid is a substrate for Qβ replicase.

14. An amplifiable nucleic acid of claim 1 further comprising a plurality of polylinkers separate from said functional nucleotide sequence and said at least one spacer element, and wherein said plurality of polylinkers are internal to said replicable nucleic acid substrate.

15. A library of amplifiable nucleic acids of claim 11 further comprising a plurality of polylinkers separate from said functional nucleotide sequence and said at least one spacer element, and wherein the plurality of polylinkers are internal to said replicable nucleic acid substrate.

16. A method for making a library of the amplifiable nucleic acids of claim 11 comprising the steps of:
 (a) synthesizing a plurality of DNA oligonucleotides comprising a first polylinker, a first randomly generated spacer element, a functional nucleotide sequence, a second randomly generated spacer element, and a second polylinker;
 (b) incorporating said DNA oligonucleotides into replicable nucleic acid substrates to form amplifiable nucleic acids; and
 (c) incorporating the resulting amplifiable nucleic acids into vector hosts.

17. The method for making a library of the amplifiable nucleic acids of claim 16 further comprising the steps of:
 (a) transforming the vectors resulting from step (c) into host cells; and
 (b) plating the transformed cells on selective plates.

18. A method for making a library of the amplifiable nucleic acids of claim 11 comprising the steps of:
 (a) synthesizing a plurality of DNA oligonucleotides comprising a first polylinker, a first randomly generated spacer element, a utility sequence of nucleotides comprising a removable subsequence of nucleotides, a second randomly generated spacer element, and a second polylinker;
 (b) incorporating said DNA oligonucleotides into replicable nucleic acid substrates to form amplifiable nucleic acids;
 (c) incorporating the resulting amplifiable nucleic acids into vector hosts;
 (d) removing the removable subsequence from the utility sequence; and
 (e) incorporating a functional nucleic acid sequence into the amplifiable nucleic acids in place of the removable subsequence.

19. The method for making a library of the amplifiable nucleic acids of claim 18 further comprising the steps of:
 (a) transforming the vectors resulting from step (e) into host cells; and
 (b) plating the transformed cells on selective plates.

20. A recombinant molecule comprising a functional nucleotide sequence flanked on each of its 3' and 5' sides by a spacer element comprising a sequence of random nucleotides and a plurality of polylinkers separate therefrom and wherein the functional nucleotide sequence and flanking spacer elements, and the plurality of polylinkers are internal to said recombinant molecule.

21. A library of recombinant molecules wherein each of said recombinant molecules comprises a functional nucleotide sequence flanked on each of its 3' and 5' sides by a spacer element comprising a sequence of random nucleotides and a plurality of polylinkers separate therefrom and wherein the functional nucleotide sequence and flanking spacer elements, and the plurality of polylinkers are internal to said recombinant molecules.

* * * * *